United States Patent
Felder et al.

(10) Patent No.: US 9,750,660 B2
(45) Date of Patent: Sep. 5, 2017

(54) DEVICES AND METHODS FOR THE TREATMENT OF METABOLIC DISORDERS

(75) Inventors: Kevin D. Felder, Cincinnati, OH (US); Mark S. Ortiz, Milford, OH (US); Alessandro Pastorelli, Rome (IT); Michele D' Arcangelo, Rome (IT); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 231 days.

(21) Appl. No.: 13/825,452

(22) PCT Filed: Mar. 30, 2012

(86) PCT No.: PCT/EP2012/055844
§ 371 (c)(1),
(2), (4) Date: Apr. 24, 2014

(87) PCT Pub. No.: WO2013/143612
PCT Pub. Date: Oct. 3, 2013

(65) Prior Publication Data
US 2015/0011919 A1    Jan. 8, 2015

(51) Int. Cl.
*A61H 9/00* (2006.01)
*A61H 23/00* (2006.01)
*A61F 5/00* (2006.01)

(52) U.S. Cl.
CPC ............. *A61H 23/00* (2013.01); *A61F 5/004* (2013.01); *A61F 5/0053* (2013.01);
(Continued)

(58) Field of Classification Search
CPC ........ A61H 9/00; A61H 9/0007; A61H 9/005; A61H 9/0071; A61H 9/0078;
(Continued)

(56) References Cited

U.S. PATENT DOCUMENTS

| 4,925,446 A * | 5/1990 | Garay | A61F 5/003 128/899 |
| 2005/0090873 A1* | 4/2005 | Imran | A61N 1/36007 607/40 |

(Continued)

FOREIGN PATENT DOCUMENTS

| WO | 2008/109300 A2 | 9/2008 |
| WO | 2009/029228 A2 | 3/2009 |

(Continued)

OTHER PUBLICATIONS

International Search Report and Written Opinion for PCT Application No. PCT/EP2012/055844, mailed Oct. 23, 2012 (17 pages).

*Primary Examiner* — Justine Yu
*Assistant Examiner* — Michael Tsai
(74) *Attorney, Agent, or Firm* — Mintz Levin Cohn Ferris Glovsky and Popeo, P.C.

(57) ABSTRACT

A system for stimulating the release of satiety hormone in a subject comprises a stimulus device (1) having a tissue engaging portion (2) intended to be placed in contact with a target tissue (3) of a gastrointestinal system of the subject, a movement device (15) linked with the tissue engaging portion (2) and operable to move the tissue engaging portion (2), thereby mechanically stimulating the target tissue (3), and an anchoring device for permanently fastening the stimulus device (1) in a target location at the gastrointestinal system such that the tissue engaging portion (2) engages the target tissue (3).

25 Claims, 14 Drawing Sheets

(52) U.S. Cl.
CPC .......... *A61F 5/0063* (2013.01); *A61F 5/0076* (2013.01); *A61F 5/0079* (2013.01)

(58) Field of Classification Search
CPC ..... A61H 9/0085; A61H 9/0092; A61F 5/003; A61F 5/0033; A61F 5/0036; A61F 5/004; A61F 5/0069; A61F 5/0076; A61F 5/0079; A61F 5/0083
See application file for complete search history.

(56) References Cited

U.S. PATENT DOCUMENTS

| | | | |
|---|---|---|---|
| 2007/0293885 A1* | 12/2007 | Binmoeller | A61F 5/0076 606/191 |
| 2009/0093839 A1* | 4/2009 | Kelleher | A61F 2/04 606/192 |
| 2010/0056948 A1 | 3/2010 | Hornby et al. | |
| 2010/0217071 A1 | 8/2010 | Ricol | |
| 2012/0004676 A1* | 1/2012 | Vargas | A61F 5/0076 606/153 |

FOREIGN PATENT DOCUMENTS

| | | | |
|---|---|---|---|
| WO | 2009/096857 A1 | 8/2009 | |
| WO | 2010/068467 A1 | 6/2010 | |
| WO | 2011/149885 A2 | 12/2011 | |

\* cited by examiner

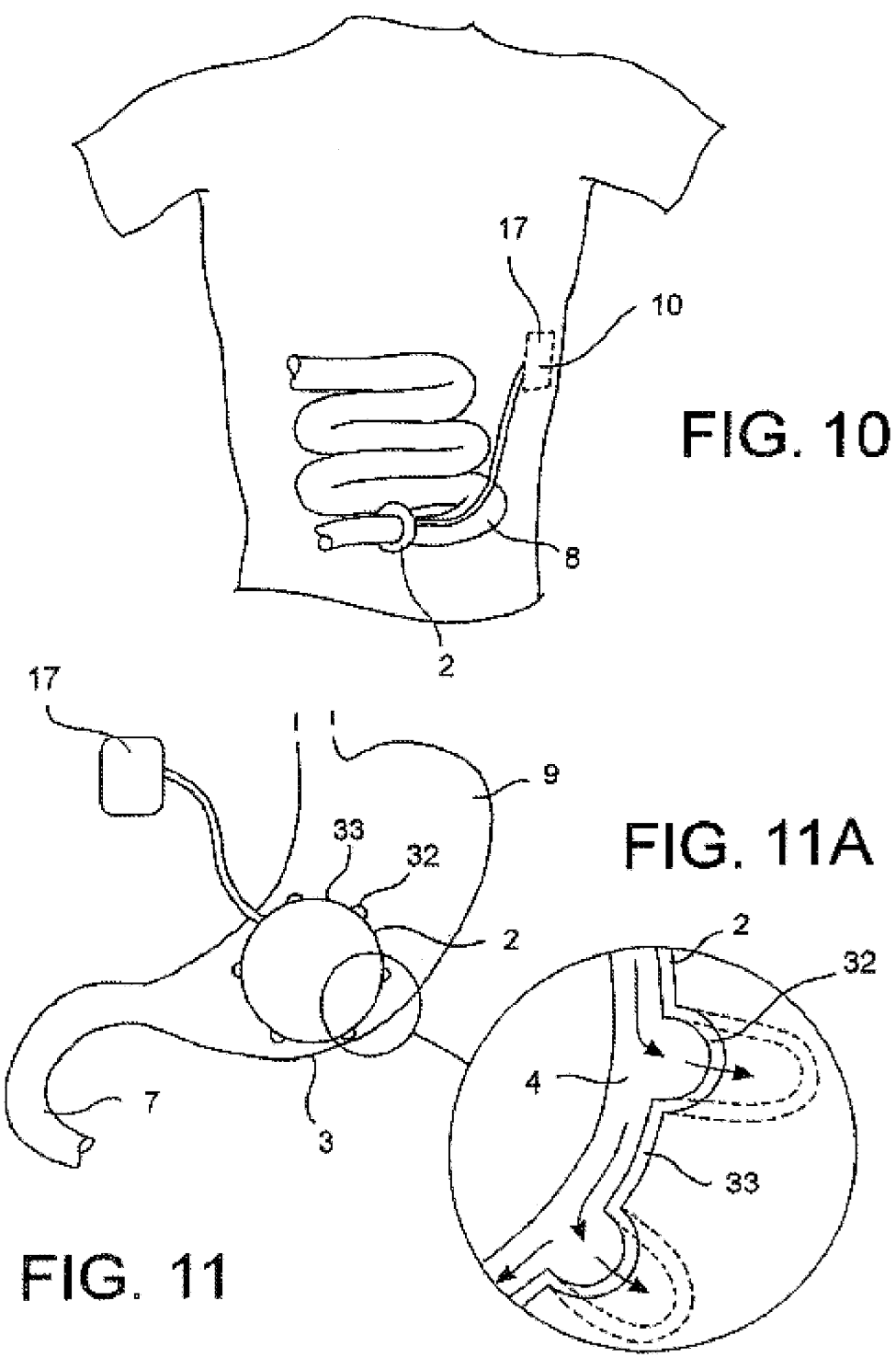

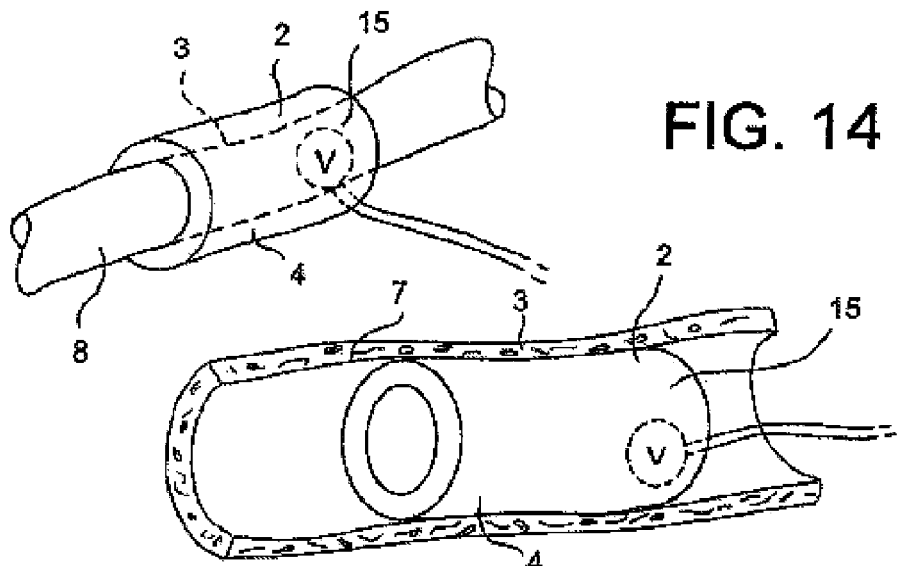
FIG. 14
FIG. 15
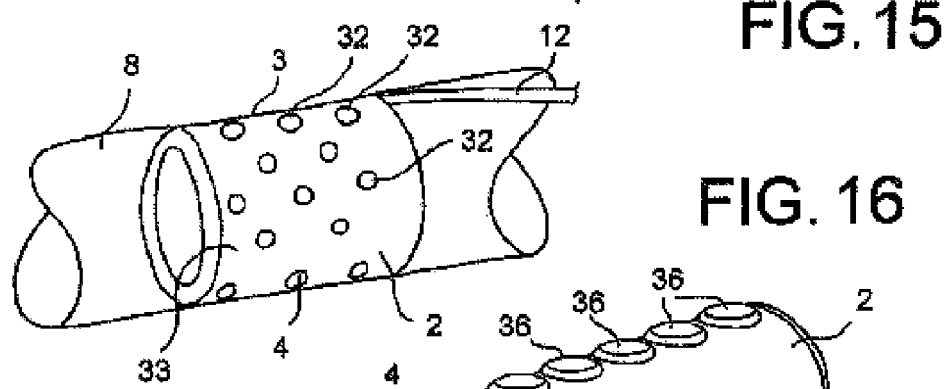
FIG. 16
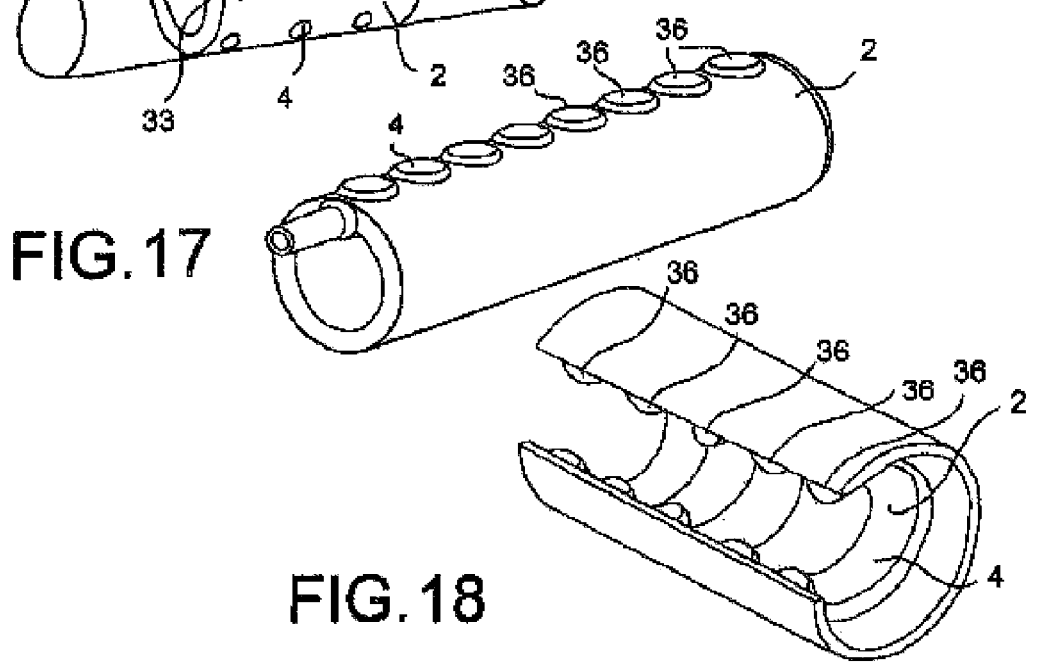
FIG. 17
FIG. 18

DEVICES AND METHODS FOR THE TREATMENT OF METABOLIC DISORDERS

FIELD OF THE INVENTION

The present invention relates generally to devices and methods for the treatment of metabolic disorders using stimulation of the gastrointestinal tract. More specifically, the present invention relates to devices and methods for stimulating the intestine in order to trigger metabolic effects. The present invention further relates to a combined system for meal detection and stimulation of the small intestine (duodenum, jejunum or ileum) aiming at an increased secretion of endogenous GLP-1 during meal intake.

BACKGROUND OF THE INVENTION

The human ability to store excess energy has contributed to an increased frequency of morbidly obese patients and those with Type 2 Diabetes. Patients having such conditions have increased morbidity and mortality resulting from associated co-morbidities, including cardiovascular disease and arthritis.

A sufficient release of Glucagon-Like Peptide (GLP-1), a known key hormone that regulates the body's glucose control hormone, is believed to alleviate Type 2 Diabetes and obesity. Normally, the presence of nutrients, which arise from a meal consisting of carbohydrates, fats and proteins, termed 'digesta' in the digestive tract, stimulates release of the body's own GLP-1 key hormone into the blood stream. Key hormones, released by specialized L-cells located in the mucosa, which is the innermost interior (luminal) wall of the intestines, coordinate the body's response to a meal. The hormones produce this effect by inducing a sense of fullness and cessation of eating (satiety), triggering the release of insulin to maintain proper glucose levels (incretin effect) and slowing the passage of contents through the digestive tract (delaying gastric emptying and slowing small intestinal transit). Altogether, these effects have been referred to as the "ileal brake" mechanism which involves both the hormones that play a role (such as PYY, GLP-1, and GLP-2, among others), as well as the multiplicity of effects of release of those hormones (gastric emptying, a feeling of fullness cessation of eating, triggering of insulin secretion).

An insufficient ileal brake, i.e., the inability of the body to release sufficient quantities of these hormones in response to a meal, is a contributory factor in obesity and Type 2 Diabetes. While in non-obese non-diabetic individuals fasting levels of GLP-1 are observed to be in the range of 5-10 pmol/L and to increase rapidly to 15-50 pmol/L after a meal, in T2D patients, the meal-related increase in GLP-1 is significantly less. The decreased insulin levels of such patients are attributable to an insufficient level of GLP-1. Similarly, also in obese subjects lower basal fasting hormone levels and smaller meal-associated rise of the hormone levels have been observed. Therefore, enhancing the body's endogenous levels of GLP-1 is believed to have impact on both obesity and diabetes.

There are known pharmaceutical means to increasing the endogenous active forms of GLP-1, e.g. by inhibition of its breakdown by dipeptidyl peptidase-4 (DPP-4) inhibitors, such as vildagliptin. In diabetic patients, improvement in glucose control is obtained by increasing the circulating levels of GLP-1 by vildagliptin.

As an alternative to pharmacological treatments, the most effective treatment for morbid obesity is bariatric surgery. A number of studies in patients after bariatric surgery suggest that there are increases in meal-related circulating GLP-1 levels after surgery, which contribute to the improvements in T2D and weight loss noted. However, bariatric surgery is perceived as a highly invasive measure recommended only for morbidly obese patients. A less invasive approach using a duodenal impermeable sleeve placed via an endoscope and fastened e.g. with a barbed metal anchor at the duodenal entrance has also shown to improve the glucose control.

It has been hypothesized that the manipulation of the intestine during and after surgery resulted in a stimulation of the mucosa which resulted in an increased release of the satiety hormone(s). US2010/0056948 describes a method of stimulating the release of satiety hormones in a subject comprising applying an electrical stimulus to a tissue in the gastrointestinal system of the subject contemporaneously with the contacting of L-cells of the tissue with a nutrient stimulus.

However, there remains still a need of improved methods and devices for stimulating the gastrointestinal system which better address the patients' fear of surgery, which are less invasive and which assure an improved patient comfort during treatment. Moreover, there is a need of improved methods and devices for accessing the stimulation site in the GI system, as well as for positioning and anchoring stimulus equipment on the patient. Further there is a need of improved methods and devices for an easier adaption of the stimulation to the specific metabolic disease and organic situation of a patient, as well as to any desired therapeutic treatment plan.

Further there is a need to provide alternatives to an electrical stimulation of the GI system.

SUMMARY OF THE INVENTION

In an aspect of the invention there is provided a method of stimulating the release of satiety hormone in a subject, the method comprising providing a stimulus device having a tissue engaging portion, placing the stimulus device in a target location of a gastrointestinal system of the subject such that the engaging portion engage a tissue of the gastrointestinal system, and moving the tissue engaging portion, thereby deforming the tissue of the GI system.

In an aspect of the invention, the step of moving the tissue engaging portion comprises moving the tissue engaging portion in an alternating manner, thereby alternatingly deforming the tissue of the GI system.

In an aspect of the invention, the step of moving the tissue engaging portion comprises alternatingly expanding and contracting the tissue engaging portion, thereby alternatingly deforming the tissue of the GI system.

In a yet further aspect of the invention, the step of moving the tissue engaging portion comprises vibrating the tissue engaging portion, thereby applying a vibrational stimulus to the tissue of the GI system.

In accordance with an aspect of the invention, the step of moving the tissue engaging portion comprises deforming the tissue engaging portion by pumping a fluid into an inflation chamber formed inside the tissue engaging portion.

In accordance with a yet further aspect of the invention, the step of moving the tissue engaging portion comprises deforming the tissue engaging portion by deforming a first articulated linkage arranged inside the tissue engaging portion.

In accordance with a yet further aspect of the invention, the step of moving the tissue engaging portion comprises deforming the tissue engaging portion by rotating a cam connected to the tissue engaging portion.

In accordance with a yet further aspect of the invention, the step of moving the tissue engaging portion comprises deforming the tissue engaging portion by heating and cooling a shape memory alloy frame connected to the tissue engaging portion.

In accordance with a yet further aspect of the invention, the step of moving the tissue engaging portion comprises deforming the tissue engaging portion by alternatingly energizing a piezoelectric oscillator connected to the tissue engaging portion.

In accordance with a yet further aspect of the invention, the step of moving the tissue engaging portion comprises connecting a magnetically attractable element to the tissue engaging portion and exposing the magnetically attractable element to a magnetic field.

In accordance with a further aspect, the method comprises endoluminally transporting the stimulus device to the target location in a gastrointestinal system of the subject and anchoring the stimulus device inside a lumen of intestine such that the engaging portion contacts an intestinal mucosa.

In accordance with a further aspect, the method comprises fixating the stimulus device from the outside to a target lumen of intestine such that the engaging portion contacts said target lumen from outside.

In accordance with a further aspect, the method comprises continuously monitoring at least one physiological characteristic of the subject to detect an ingestion of food by the subject, and moving the tissue engaging portion in response to a detected ingestion of food.

In accordance with an aspect, the method comprises:
arranging a compressible fluid chamber at a lumen wall of the gastrointestinal system such that a hoop deformation, i.e. expansion or contraction, of the lumen wall, brings about a volume change of the fluid chamber,
putting the fluid chamber in fluidic communication with an inflation chamber formed inside the tissue engaging portion.

In accordance with a yet further aspect, the method comprises:
arranging a second articulated linkage at a lumen wall of the gastrointestinal system such that a hoop deformation, i.e. expansion or contraction, of the lumen wall, brings about a shape change of the second articulated linkage;
connecting the second articulated linkage by a movement transmitting link with a first articulated linkage of the movement device such that the shape change of the second articulated linkage brings about a shape change of the first articulated linkage and, hence, a stimulation of the target tissue.

In accordance with a further aspect of the invention, a system is provided for stimulating the release of satiety hormone in a subject, the system comprising a stimulus device having:
a tissue engaging portion intended to be placed in contact with a target tissue of a gastrointestinal system of the subject;
a movement device linked with the tissue engaging portion and operable to move the tissue engaging portion, thereby mechanically stimulating the target tissue;
wherein the system further comprises means for permanently anchoring the stimulus device in a target location at the gastrointestinal system such that the tissue engaging portion engages the target tissue.

In an aspect of the invention, the movement device is configured to move the tissue engaging portion in an alternating manner, thereby alternatingly deforming the target tissue of the GI system.

In accordance with a further aspect of the invention, the movement device is configured to alternatingly expanding and contracting the tissue engaging portion, thereby alternatingly deforming the tissue of the GI system.

In a yet further aspect of the invention, the movement device is configured to make the tissue engaging portion vibrate, thereby applying a vibrational stimulus to the tissue of the GI system.

In accordance with an aspect of the invention, the movement device comprises a pump adapted to pump a fluid into an inflation chamber formed inside the tissue engaging portion.

In accordance with a yet further aspect of the invention, the movement device comprises an articulated linkage arranged inside the tissue engaging portion.

In accordance with a yet further aspect of the invention, the movement device comprises a cam connected to the tissue engaging portion, and a motor for rotating the cam.

In accordance with a yet further aspect of the invention, the movement device comprises a shape memory alloy frame connected to the tissue engaging portion and a heater arranged to heat the shape memory alloy frame and bring about transition between at least two different shapes of the frame.

In accordance with a yet further aspect of the invention, the movement device comprises a piezoelectric oscillator connected to the tissue engaging portion.

In accordance with a yet further aspect of the invention, the movement device comprises a magnetically attractable element connected to the tissue engaging portion and a magnetic field source adapted to displace the magnetically attractable element, thereby moving the tissue engaging portion.

In accordance with a further aspect, the stimulus device is adapted for endoluminal transportation to the target location in a gastrointestinal system.

In accordance with a further aspect, the stimulus device is adapted to be fixated from the outside to a target lumen of intestine and the engaging portion is arranged for contacting the target lumen from outside.

In accordance with a yet further aspect of the invention, the stimulus system comprises a detection device which is implantable in the subject and adapted to continuously monitoring at least one physiological characteristic of the subject to detect an ingestion of food by the subject, and the detection device cooperates with the stimulus device such that the stimulus device moves the tissue engaging portion in response to a detected ingestion of food.

In accordance with an aspect, the detection device comprises a compressible fluid chamber which is configured and connectable to a lumen wall of a gastrointestinal system such that a hoop deformation, i.e. expansion or contraction, of the lumen wall, brings about a volume change of the fluid chamber, the fluid chamber forming part of a pump in fluidic communication with an inflation chamber formed inside the tissue engaging portion.

In accordance with an aspect, the detection device comprises a second articulated linkage connected by a movement transmitting link with a first articulated linkage of the movement device, in which the second articulated linkage is configured and connectable to a lumen wall of a gastrointestinal system such that a hoop deformation, i.e. expansion or contraction, of the lumen wall, brings about a shape change of the second articulated linkage and a displacement of the movement transmitting link.

These and other aspects and advantages of the present invention shall be made apparent from the accompanying drawings and the description thereof, which illustrate embodiments of the invention and, together with the general description of the invention given above, and the detailed description of the embodiments given below, serve to explain the principles of the present invention.

BRIEF DESCRIPTION OF THE DRAWINGS

FIG. 10 shows a system and method for stimulating the release of satiety hormones in accordance with a yet further embodiment;

FIGS. 11 and 11A illustrate a stimulus device of the stimulus system and a detail of a tissue engaging portion of the stimulus device in accordance with an embodiment;

FIG. 14 illustrates a stimulus device and method step in accordance with a further embodiment;

FIG. 15 illustrates a stimulus device and method step in accordance with a further embodiment;

FIGS. 16, 17, 18 illustrate a stimulus devices in accordance with further embodiments;

DETAILED DESCRIPTION OF EMBODIMENTS

Figure 1:
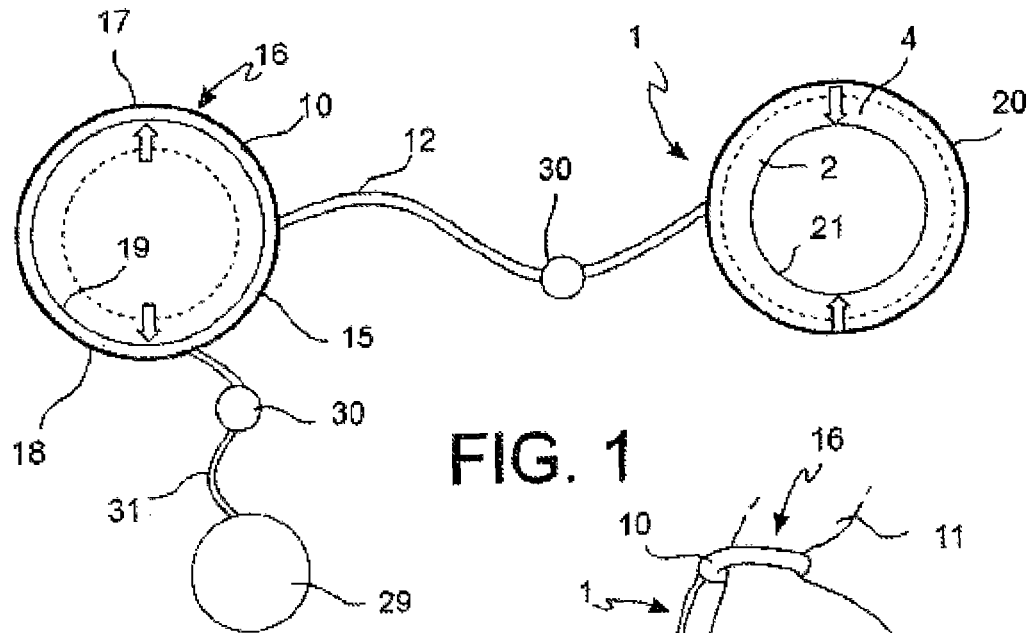
FIG. 1 shows a system for stimulating the release of satiety hormones in accordance with an embodiment.

Referring to the drawings in which like numerals denote like anatomical structures and components throughout the several views, methods and devices are provided for stimulating the release of satiety hormone, specifically GLP-1, in a human subject.

In accordance with a first aspect of the invention, there is provided a method of stimulating the release of satiety hormone in a subject, the method comprising providing a stimulus device 1 having a tissue engaging portion 2, placing the stimulus device 1 in a target location of a gastrointestinal system of the subject such that the engaging portion 2 engages a target tissue 3, e.g. mucosa, of the gastrointestinal system, and moving the tissue engaging portion 2, thereby deforming and mechanically stimulating the target tissue 3 of the GI system.

In accordance with an embodiment, the step of moving the tissue engaging portion 2 may comprise moving the tissue engaging portion 2 in an alternating manner, e.g. alternatingly expanding and contracting the tissue engaging portion 2, thereby alternatingly deforming, e.g. expanding and contracting, the target tissue 3 of the GI system.

In a further embodiment, the tissue engaging portion 2 may be made vibrate, thereby applying a vibrational stimulus to the target tissue 3 of the GI system.

The step of moving the tissue engaging portion 2 may be accomplished by deforming the tissue engaging portion 2 by pumping a fluid, e.g. saline solution, $CO_2$, air, into an inflation chamber 4 formed inside the tissue engaging portion 2.

Alternatively, the tissue engaging portion 2 may be moved and deformed by deforming a first articulated linkage 5 arranged inside the tissue engaging portion 2 or connected thereto.

In accordance with a yet further embodiment, the step of moving the tissue engaging portion 2 comprises rotating a cam or an eccentric which is received inside or connected to the tissue engaging portion 2.

In a yet further exemplary embodiment, the tissue engaging portion 2 is deformed by heating and cooling a shape memory alloy frame 6 connected to or received inside the tissue engaging portion 2.

In a yet further embodiment, the tissue engaging portion 2 may be deformed by alternatingly energizing a piezoelectric oscillator connected to the tissue engaging portion.

In a further embodiment, the step of moving the tissue engaging portion 2 comprises connecting a magnetically attractable element to the tissue engaging portion and exposing the magnetically attractable element to an alternating or continuous magnetic field.

All described method steps for moving and/or deforming the tissue engaging portion 2 (in order to move and/or deform the target tissue 3) can be performed in an intermittent or pulsing or alternating manner such as to apply an oscillating mechanical stimulus to the target tissue 3 for an increased release of satiety hormone, particularly GLP-1.

Advantageously, the stimulus device 1 is endoluminally, e.g. transorally or transanally, transported to the target location, e.g. duodenum 7, ileum 8 or stomach 9, in the gastrointestinal system of the subject and anchored inside a lumen of intestine such that the engaging portion 2 contacts and, hence, mechanically stimulates an intestinal mucosa to release GLP-1.

Alternatively, placement of the stimulus device 1 may be effected by open surgery or by laparoscopy, but also by endolumenal transportation of the stimulus device 1 to the desired site for stimulating the production of GLP-1, translumenal placement of the stimulus device 1 from inside the intestine through an incision in the lumen wall to its outside and fixation to an external side of the target lumen such that the tissue engaging portion 2 contacts the target lumen from outside.

In accordance with an embodiment, the method comprises continuously monitoring at least one physiological characteristic of the subject to detect an ingestion of food by the subject, and moving the tissue engaging portion 2 in response to a detected ingestion of food. For this purpose, an esophageal or duodenal wall movement, particularly hoop expansion, or a gastric wall contraction or a gastric pH may be detected.

In an exemplary embodiment, a compressible fluid chamber 10 may be arranged at a lumen wall of the gastrointestinal system where it is desired to detect a passage of food, particularly the fluid chamber 10 may be extended around a section of esophagus 11, around a section of duodenum 7 or placed inside a stomach 9, such that a hoop deformation, i.e. expansion or contraction, of the lumen wall, brings about a volume change of the fluid chamber 10. The fluid chamber 10 can be put in fluidic communication with the inflation chamber 4 formed inside the tissue engaging portion 2 of the stimulus device 1. In this manner, the compressible fluid chamber 10 acts both as food detecting device 16 and as pump 17 which changes the shape of the tissue engaging portion 2 in response to a hoop deformation of the section of GI tract where the food passage is detected.

In a further embodiment, a second articulated linkage 13 may be arranged at a lumen wall of the gastrointestinal system where it is desired to detect a passage of food, particularly the second articulated linkage 13 may be placed inside the stomach 9, such that a gastric contraction brings about a shape change of the second articulated linkage 13. The second articulated linkage 13 can be connected to the first articulated linkage 5 of the tissue engaging portion 2 by means of a movement transmitting link 14, e.g. a pull cable, a push-pull rod or a Bowden cable, such that the shape change of the second articulated linkage 13 brings about a shape change of the first articulated linkage 5 at the tissue engaging portion 2 and, hence, a mechanical stimulation of the target tissue 3.

In accordance with a second aspect of the invention, there is provided a system for stimulating the release of satiety hormone in a subject, the system comprising a stimulus device 1 having a tissue engaging portion 2 intended to be placed in contact with a target tissue 3 of a gastrointestinal system of the subject, a movement device 15 linked with the tissue engaging portion 2 and operable to move the tissue engaging portion 2, thereby mechanically stimulating the target tissue 3. The system further comprises means for permanently anchoring the stimulus device 1 in a target location at the gastrointestinal system such that the tissue engaging portion 2 engages the target tissue 3. The movement device 15 may be configured to move the tissue engaging portion 2 in an alternating manner, thereby alternatingly deforming the target tissue 3 of the GI system. For instance, the movement device 15 may be configured to alternatingly expanding and contracting the tissue engaging portion 2, thereby alternatingly expanding or contracting a target tissue 3. In an embodiment, the movement device 15 may be configured to make the tissue engaging portion 2 vibrate, thereby applying a vibrational stimulus to the target tissue 3.

In accordance with a further embodiment, the stimulus system comprises a detection device 16 which is implantable in the subject and adapted to continuously monitoring at least one physiological characteristic of the subject to detect an ingestion of food by the subject. The detection device 16 cooperates with the stimulus device 1 such that the stimulus device 1 moves the tissue engaging portion 2 (and stimulates the release of GLP-1) in response to a detected ingestion of food.

In accordance with an embodiment (FIGS. 1 to 19) the movement device 15 comprises a pump 17 adapted to pump a fluid into an inflation chamber 4 formed inside the tissue engaging portion 2, thereby deforming the tissue engaging portion 2.

The detection device 16 may comprise a compressible fluid chamber 10 which forms part of the pump 17 and which may be in direct fluidic communication with the inflation chamber 4 formed inside the tissue engaging portion 2. The compressible fluid chamber 10 is connectable to a lumen wall of the gastrointestinal system and configured such that a hoop deformation, i.e. expansion or contraction, of the lumen wall brings about a volume change of the fluid chamber 10 which in turn pumps the fluid into the inflation chamber 4.

In an embodiment (FIG. 1), the compressible fluid chamber 10 has an arch or ring shaped configuration or is adapted to be locked in an arch or ring shaped configuration and comprises a substantially inextensible radially outer wall 18 and a foldable or extensible radially inner wall 19 such that a displacement of the inner wall 19 in a radially outward direction approximates the inner wall 19 towards the outer wall 18 which doesn't expand. Hence, an internal volume of the compressible fluid chamber 10 is reduced and the exceeding fluid is pushed through a flexible fluid duct 12 from the compressible fluid chamber 10 of the detection device 16 in the inflatable chamber 4 of the tissue engaging portion 2.

Also the inflatable chamber 4 of the tissue engaging portion 2 may have an arch or ring shape or may be adapted to be locked in an arch or ring shaped configuration and comprises a substantially inextensible radially outer wall 20 and a foldable or extensible radially inner wall 21 such that an increase of the internal volume of the inflation chamber 4 (due to the excess fluid pumped from the fluid chamber 10 into it) displaces the inner wall 21 in a radially inward direction and away from the outer wall 20 which doesn't expand.

Figure 2:
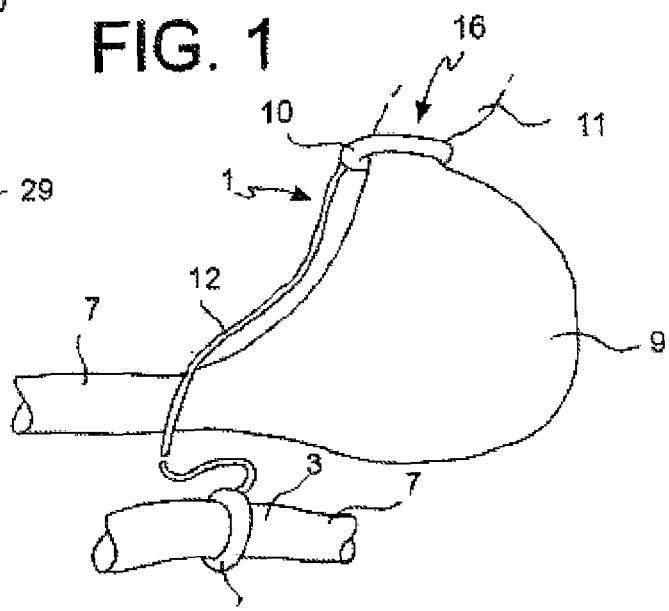
FIGS. 2 and 3 illustrate methods for stimulating the release of satiety hormone involving the system in FIG. 1.
Figure 3:
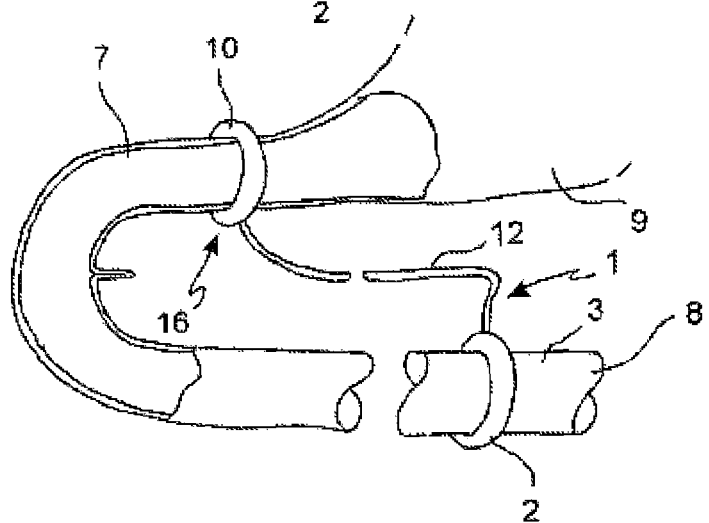
Figure 4:
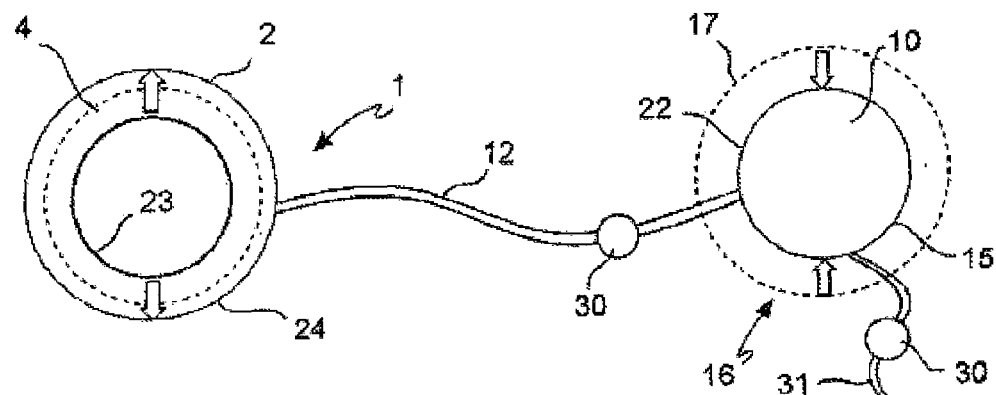
FIG. 4 shows a system for stimulating the release of satiety hormones in accordance with a further embodiment.

As illustrated in FIGS. 2 and 3, the compressible fluid chamber 10 may be placed in the intraperitoneal space either around the esophagus 11 or around the duodenum 7 so that an expansion thereof due to the passage of a food bolus or chime triggers the above described pump activation and transfers fluid to the inflatable chamber 4 of the tissue engaging portion 2. The inflatable chamber 4 of the tissue engaging portion 2 can be placed in the intraperitoneal space around a target section of the lower intestine, e.g. duodenum 7 or ileum 8, so that inflation of the inflatable chamber 4 mechanically stimulates the release of GLP-1 in the target tissue 3.

In accordance with a further embodiment (FIGS. 4 through 7), the compressible fluid chamber 10 has a compressible balloon shape or ring shaped configuration adapted to be endoluminally inserted in the stomach 9. The compressible fluid chamber 10 comprises an elastically extensible or inextensible but foldable outer wall 22 such that a displacement of the outer wall 22 in a radially inward direction (due to stomach contraction) reduces an internal volume of the compressible fluid chamber 10 and pushes the exceeding fluid through a flexible fluid duct 12 from the compressible fluid chamber 10 of the detection device 16 in the inflatable chamber 4 of the tissue engaging portion 2.

The inflatable chamber 4 of the tissue engaging portion 2 (FIG. 4) may have a ring or tube shape adapted to be inserted in a small intestine, and comprises a substantially rigid radially inner wall 23 which defines a passage for intestinal contents, and a foldable or extensible radially outer wall 24 such that an increase of the internal volume of the inflation chamber 4 (due to the excess fluid pumped from the fluid chamber 10 into it) displaces the outer wall 24 in a radially outward direction and away from the inner wall 23 which doesn't deform.

Figure 5:
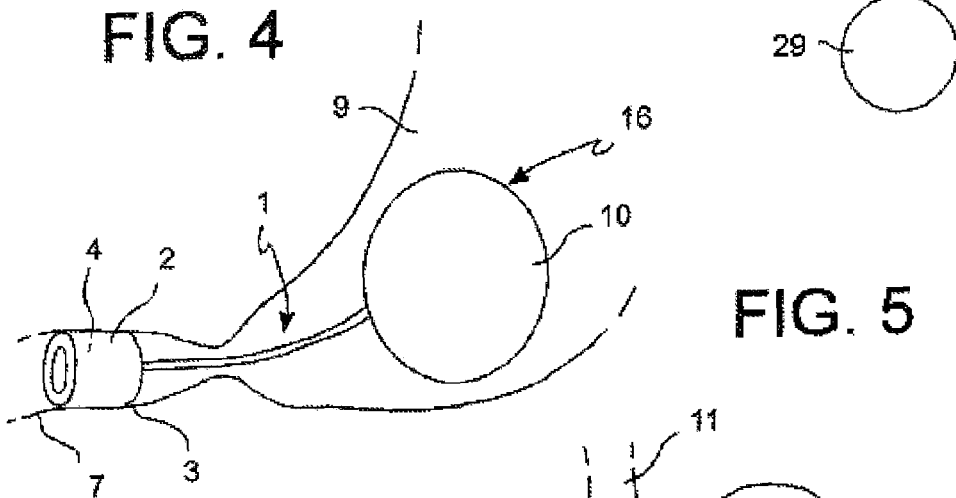
FIG. 5 illustrates a method for stimulating the release of satiety hormone involving the system in FIG. 4.
Figure 6:
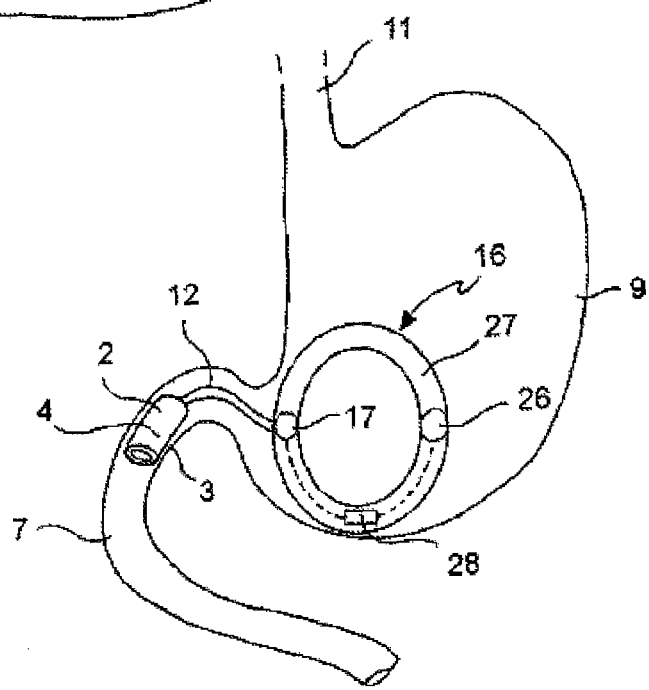
FIG. 6 shows a system and method for stimulating the release of satiety hormones in accordance with a further embodiment.

As illustrated in FIGS. 5 and 6, the compressible fluid chamber 10 may be placed in the stomach 9 so that a contraction of the stomach due to the presence of food triggers the above described pump activation and transfers fluid to the inflatable chamber 4 of the tissue engaging portion 2. The inflatable chamber 4 of the tissue engaging portion 2 can be placed endoluminally inside a target section of the lower intestine, e.g. duodenum 7 or ileum 8, so that inflation of the inflatable chamber 4 mechanically stimulates the release of GLP-1 in the target tissue 3.

Figure 7:
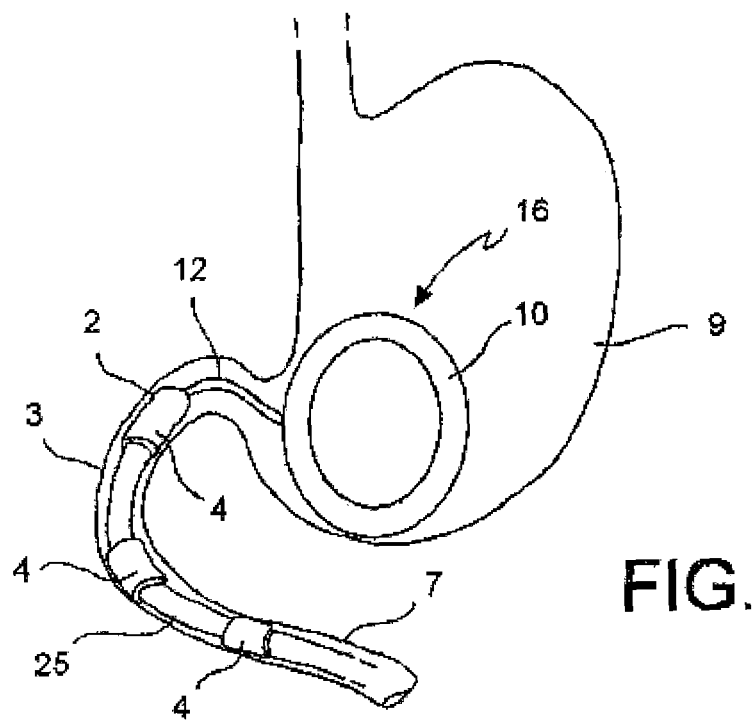
FIG. 7 shows a system and method for stimulating the release of satiety hormones in accordance with a yet further embodiment.
Figures 8, 9:
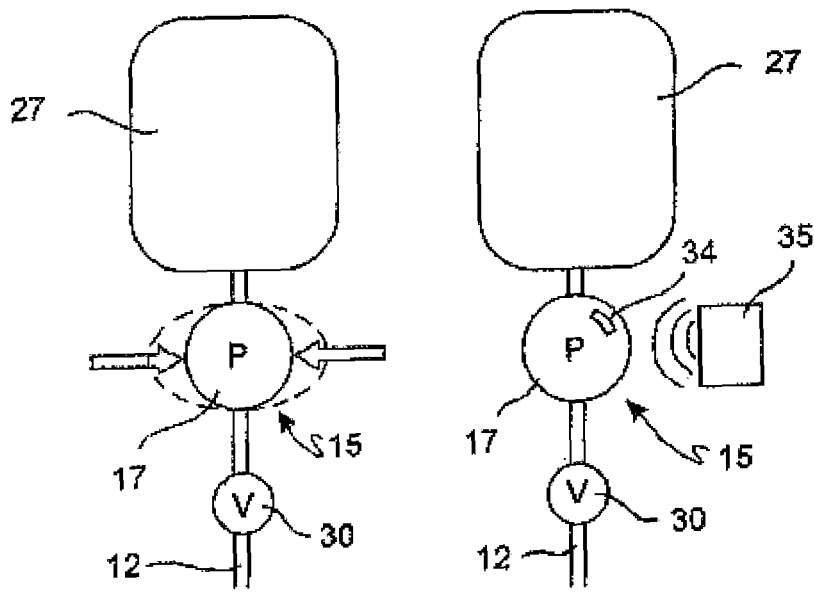
FIGS. 8 and 9 illustrate two alternative schemes of a fluid pumping device of the system in accordance with embodiments.
Figure 12:
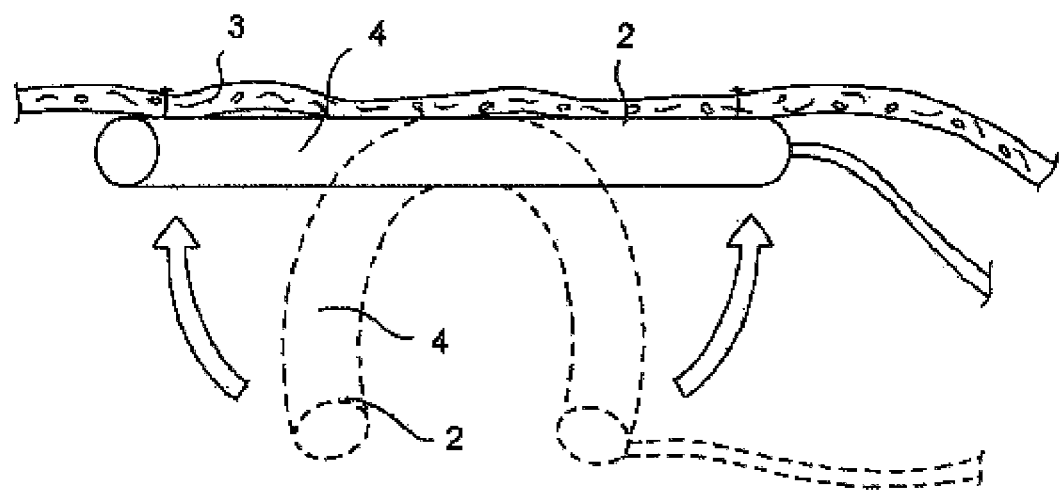
FIG. 12 illustrates a stimulus device in accordance with a further embodiment.
Figure 13:
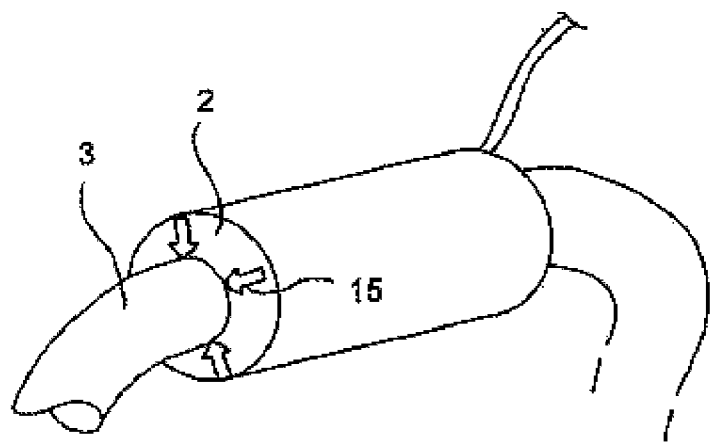
FIG. 13 illustrates a stimulus device in accordance with a further embodiment.
Figure 19:
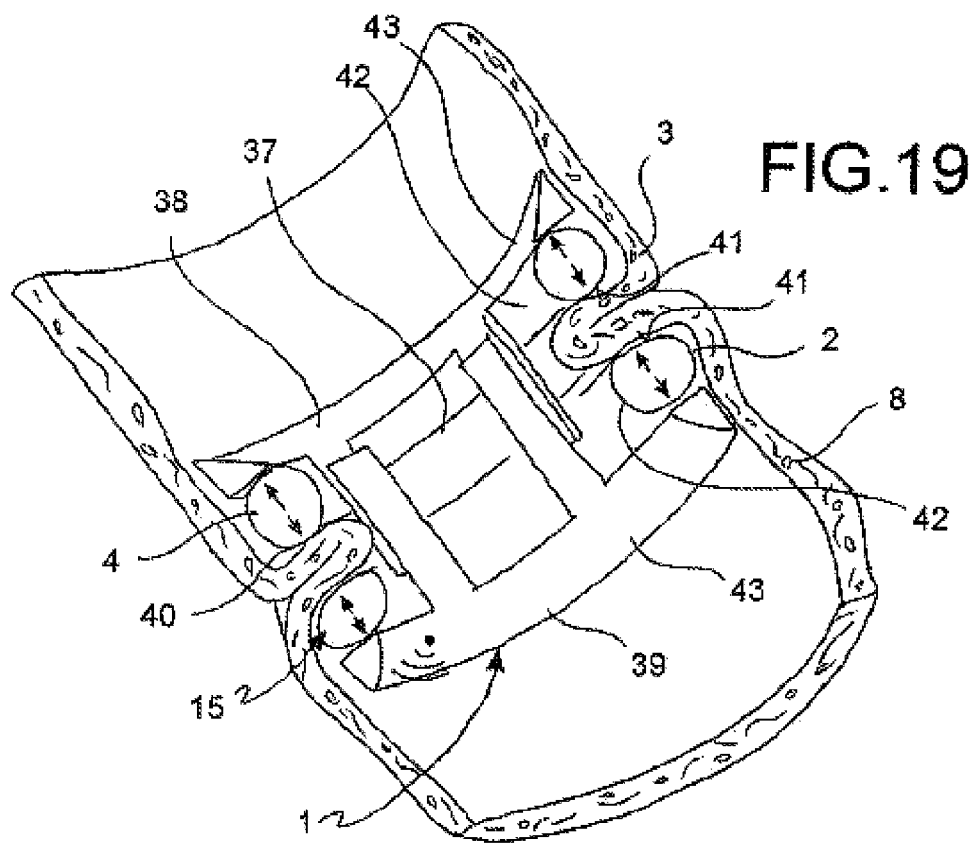
FIG. 19 illustrates a stimulus devices in accordance with a further embodiment.

As illustrated in FIG. 7, one or more inflatable chambers 4 can be arranged on a duodenal sleeve 25 which may be anchored, e.g. by the same fluid duct 12, to the gastric balloon or coil shaped detecting device 16.

In accordance with an embodiment (FIG. 6), the detection device 16 may comprise a gastric anchoring portion, e.g. an expandable coil or balloon, and house a battery powered pump 17 with a fluid reservoir 27 and a pH sensor 26, as well as a control unit 28 linked to the pH sensor 26 and to the pump 17 and adapted to activate the pump 17 in response to a detected pH, thereby transferring fluid from the reservoir 27 to the inflation chamber 4. The control unit 28 is further configured to activate the pump 17 in an opposite flow direction to transfer the fluid back into the fluid reservoir 27 after a preset stimulus time. Alternatively, the control unit 28 may be configured to dis-activate the pump 17 after a preset stimulus time, thereby allowing the fluid to flow back into the fluid reservoir 27 due to a contraction of the inflation chamber 4. The control unit 28 is programmable and allows a purposeful mechanical stimulation which doesn't depend from the intensity of the physiological gastric or intestinal movements.

In accordance with embodiments, the pump 17 may be in fluid connection with an additional fluid reservoir 29 and controllable fluid direction valves 30 (selectable one-way condition in either direction) may be arranged in the fluid duct 12 connecting the pump 17 to the inflation chamber 4 and also in a fluid duct 31 between the pump 17 and the additional reservoir 29. The valve 30 in the fluid duct 12 connecting the pump 17 to the inflation chamber 4 may be configured to release the fluid slowly back to the pump 17 and reservoir 29 (where provided). In this manner, during pumping the fluid is transferred into the tissue engaging portion 2 and after pumping stops, the fluid leaks slowly back to the pump.

In accordance with a further embodiment (FIG. 10), the pump 17 comprises a manually operable subcutaneously implantable pump, e.g. an elastically compressible fluid chamber 10 or bladder which may additionally fluid connected to a fluid reservoir 29 and which can be manually activated by extracorporeally pressing the fluid chamber 10. If required, the pump and reservoir may be refilled by the patient or doctor, e.g. by injecting air or lopamidol.

In accordance with a yet further embodiment (FIG. 9) the pump 17 may comprise a magnetically attractable component 34 adapted to drive the pump 17 in response to a magnetic field which can be generated by an extracorporeal electromagnetic field source 35.

In accordance with an embodiment (FIGS. 11A, 16), the inflation chamber 4 may comprise an external wall forming a plurality of inflatable dimples 32 or protrusions adapted to be inflated and inextensible wall regions 33 formed around the dimples 32 which do not inflate together with the dimples 32, thereby significantly reducing the change of volume and fluid required for stimulating the target tissue 3. In an embodiment, the wall thickness of the inflatable dimples 32 or protrusions is smaller than the wall thickness of the surrounding inextensible wall regions 33.

In accordance with an embodiment (FIG. 12), the tissue engaging portion 2 may have an elongate shape adapted to be extended inside a small intestine and which can be deformed by circulating a fluid therethrough, thereby activating the release of GLP-1.

Alternatively, the tissue engaging portion 2 may have an elongate shape adapted to be extended inside a small intestine and defining an internal inflation chamber 4 such that by inflating the internal inflation chamber 4 the elongate tissue engaging portion 2 straightens from a bent shape (broken line) to a straightened shape (solid line) thereby mechanically stimulating the intestine. When ends of the engaging portion 2 are fastened to a target tissue 3 of the intestine, alternating bending and straightening of the engaging portion 2 may cause an alternating contraction and stretching of the target tissue 3.

In accordance with an embodiment (FIGS. 7, 17, 18), the inflation chamber 4 defines a plurality of communicating chamber sections 36 arranged in series and adapted to inflate in a predetermined sequence in dependency of the pressure inside the inflation chamber 4.

In accordance with a yet further embodiment (FIG. 19), the tissue engaging portion 2 can be endoluminally attached to a fold or plication 37 of intestinal wall. For this purpose, the system may comprise two ring members 38, 39 connected or connectable to each other to define an externally open annular groove 40 or annular space therebetween which is adapted to receive the circumferential plication 37 of intestinal wall protruding into the intestinal lumen. At least one or both ring members 38, 39 have a pressure surface 41 which faces the other ring member and forms one of two opposite lateral faces of the annular groove 40. In this embodiment the movement device 15 is adapted to move the at least one pressure surface 41 with respect to the opposite lateral face of the annular groove 40, thereby applying or releasing a mechanical pressure on the plication 37 of intestinal wall. For this purpose at least one or both ring members 38, 39 may comprise a rigid backing ring 43 and an inflatable or otherwise expandable and retractable toroidal member 42 connected to the backing ring 43 and forming the pressure surface 41. The toroidal member 42 may be deformed, i.e. expanded and contracted, e.g. by means of any one of the previously described embodiments of pump 17 connected thereto by a fluid conduit 12. Advantageously, the two opposite inflatable toroidal members 42 are in fluidic communication to passively adapt to the tissue configuration and movements triggered by the stimulus device 1.

Alternatively or additionally, the two ring members 38, 39, particularly the rigid backing rings 43 are movable to one another, e.g. by a hydraulic, mechanical, electromechanical (screw drive), or magnetic actuator to squeeze and release the tissue plication 37, thereby stimulating the release of GLP-1. In this embodiment, the toroidal members 42 which are significantly softer than the backing rings 43 allow for a soft non-traumatic contact with the mucosa. The stimulus device 1 can be remotely controlled via RF transmission or directly linked to the detecting device 16 for a mechanical GI tissue stimulation in response to a detected ingestion of food.

Figure 21:
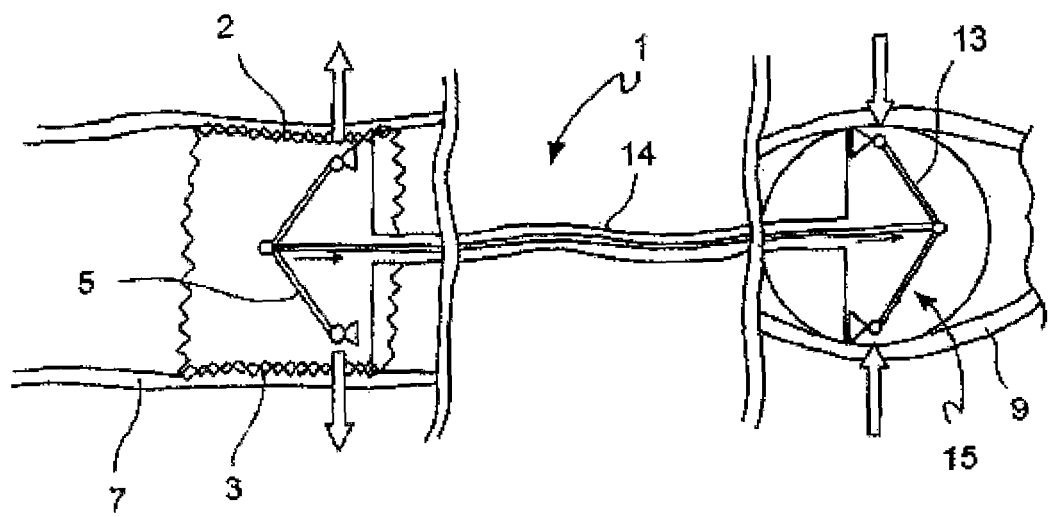
FIG. 21 shows a system and method for stimulating the release of satiety hormones, involving an articulated linkage mechanism, in accordance with a further embodiment.

In accordance with an embodiment (FIG. 21) the movement device 15 comprises a first articulated linkage 5 (e.g. an articulated four bar linkage or a two bar linkage with one hinge and slidingly constrained ends opposite the hinge) arranged inside the tissue engaging portion 2 and connected to a movement transmitting link 14, so that a (e.g. push-pull) displacement of the movement transmitting link 14 deforms the first articulated linkage 5, thereby mechanically stimulating the target tissue 3.

Analogously, the detecting device 16 may comprise a second articulated linkage 13 (e.g. an articulated four bar linkage or a two bar linkage with one hinge and slidingly constrained ends opposite the hinge) received by a (balloon or coil shaped) gastric anchoring member and connected to the movement transmitting link 14. In this manner, a compression of the anchoring member due to a gastric contraction brings about a shape change of the second articulated linkage 13 and displaces the movement transmitting link 14, e.g. a pull cable, a push-pull rod or a Bowden cable, which in turn effects a shape change (expansion) of the first articulated linkage 5 at the tissue engaging portion 2 and, hence, a mechanical stimulation of the target tissue 3.

Figure 20:
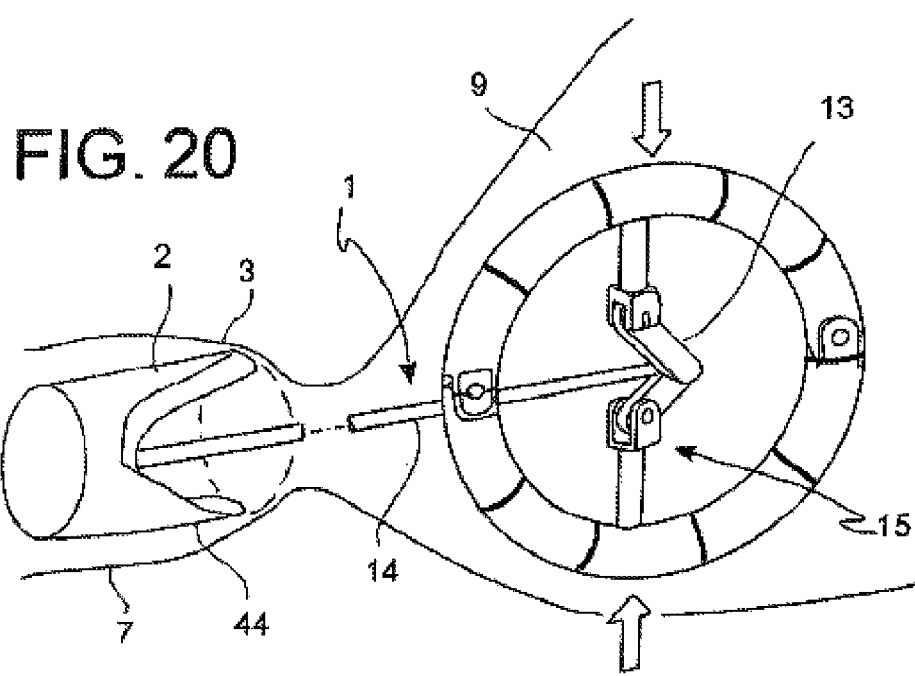
FIG. 20 shows a system and method for stimulating the release of satiety hormones, involving an articulated linkage mechanism, in accordance with an embodiment.

Alternatively, the tissue engaging portion 2 may comprise a rigid body portion 44 (FIG. 20) connected to the movement transmission link 14, preferably a pull cable, such that a pulling movement of the transmission link 14 pushes the rigid body portion 44 against the target tissue 3, e.g. against a proximal duodenum 7 near the pylorus.

Figure 22:
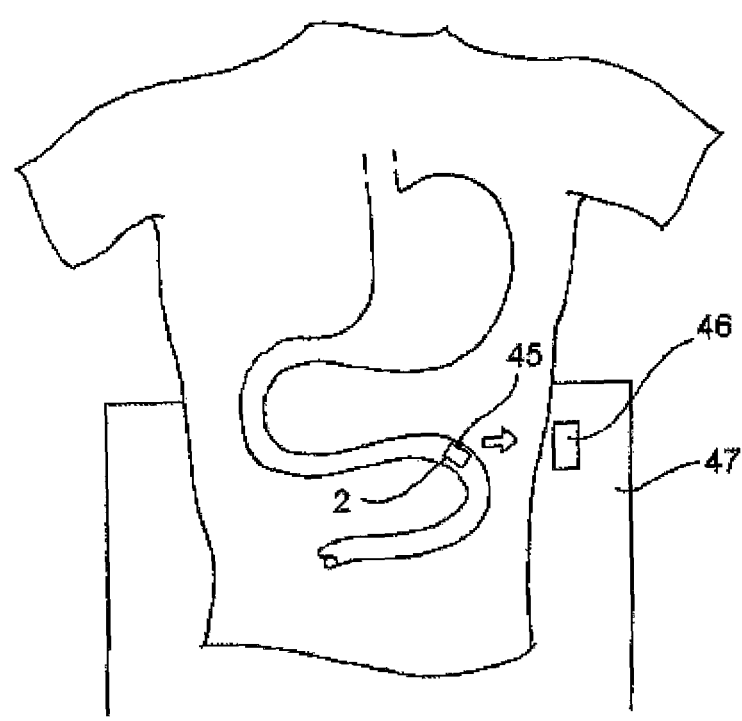
FIG. 22 shows a system and method for stimulating the release of satiety hormones, involving a magnetic movement activation, in accordance with an embodiment.
Figure 23:
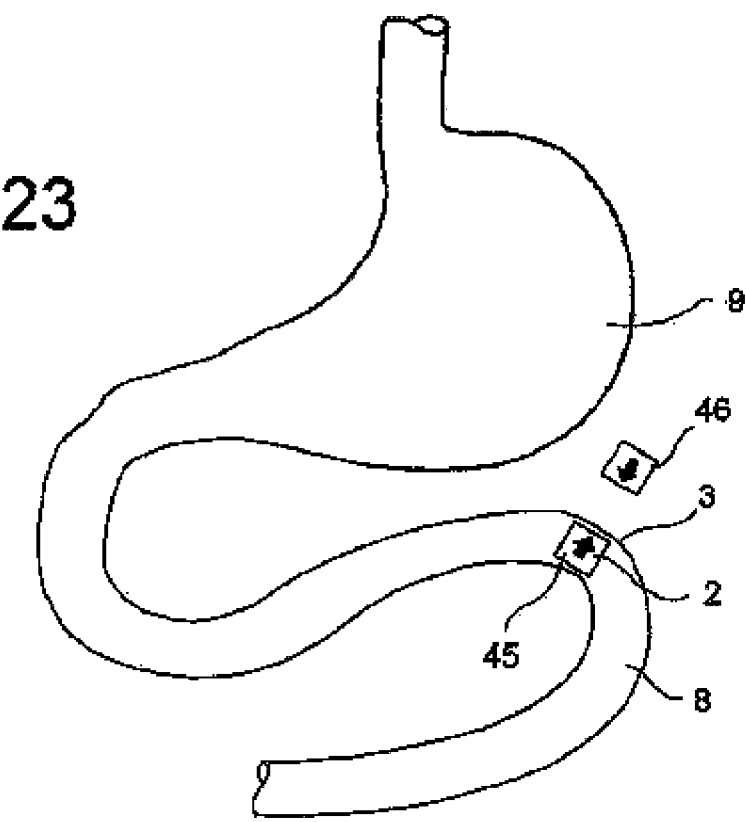
FIG. 23 shows a system and method for stimulating the release of satiety hormones, involving a magnetic movement activation, in accordance with a further embodiment.

In accordance with an embodiment (FIGS. 22, 23), the movement device 15 comprises a magnetically attractable element 45, e.g. a ferromagnetic material, connected to the tissue engaging portion 2 and a magnetic field source 46 adapted to displace the magnetically attractable element 45, thereby moving the tissue engaging portion 2 and stimulating the target tissue 3 to release GLP-1. The magnetic field source 46 may comprise an electromagnet adapted to generate a pulsing or alternating magnetic field adapted to make the tissue engaging portion 2 move in a cyclic or alternate manner. The magnetic field source may be implantable in the body of the patient (FIG. 23) or it may be configured as an extracorporeal portable or stationary device (FIG. 22) which would be easy to replace or to adjust if necessary. In some embodiments, the magnetic field source is built into a bed or chair or other patient support structure 47.

Figure 24:
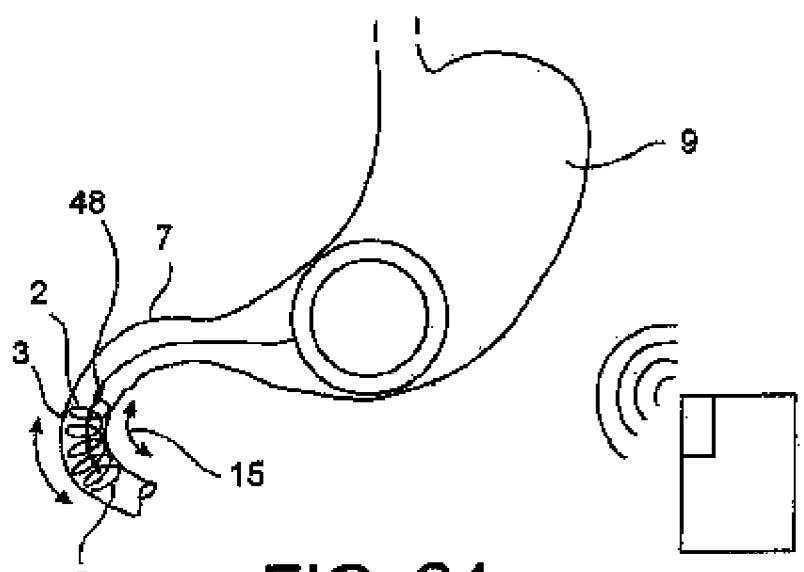
FIG. 24 shows a system and method for stimulating the release of satiety hormones, involving a shape memory alloy phase transition movement activation, in accordance with an embodiment.

In accordance with a further embodiment (FIG. 24), the movement device 15 comprises a shape memory alloy frame 6 connected to or received inside the tissue engaging portion 2 and a heater 48 arranged to heat the shape memory alloy frame 6 and bring about transition between at least two different shapes of the frame. In an embodiment the shape memory alloy frame 6 has a helix shape and is deformable between a radially expanded and a radially retracted shape phase. Alternatively, the shape memory alloy frame 6 has a helix shape and is deformable between an axially expanded and an axially retracted shape phase. The tissue engaging portion 2 can be held inside the duodenum by a tether connected to a gastric anchoring body. The heater 48 may be activated remotely through RF transmission or inductive energy transfer or by an electrical wire connection. The shape memory alloy frame 6 and heater 48 are thermally coupled to each other but they may be thermally isolated from the external environment to prevent tissue trauma.

Figure 25:
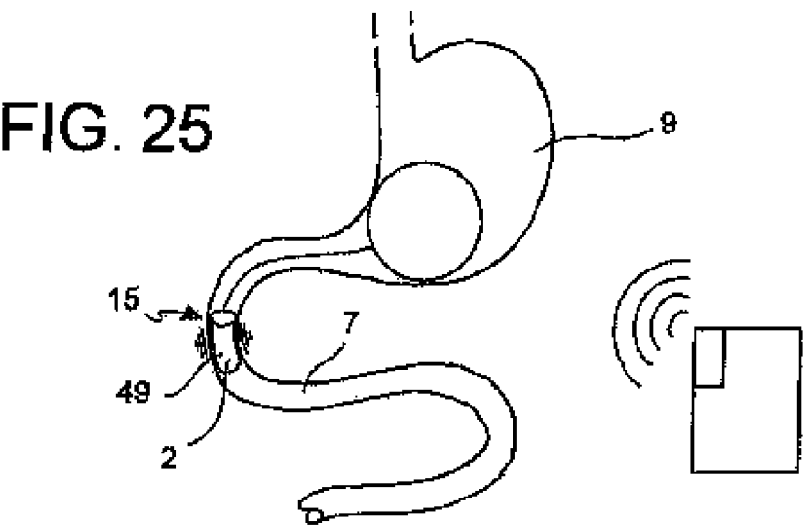
FIG. 25 shows a system and method for stimulating the release of satiety hormones, involving a piezoelectric oscillator, in accordance with an embodiment.

In accordance with an embodiment (FIG. 25), the movement device 15 comprises a vibrator, e.g. an electrically activatable piezoelectric oscillator 49 connected to the tissue engaging portion 2 or a motor driven cam or eccentric connected to the tissue engaging portion 2. The vibrator may be energized and activated remotely through RF transmission or inductive energy transfer or by an electrical wire connection.

The stimulus device 1 may be adapted for endoluminal transportation to the target location in the gastrointestinal system or, alternatively, the stimulus device 1 is adapted to be fixated from the outside to a target lumen of intestine and the tissue engaging portion 2 is arranged for contacting the target lumen from outside.

Figure 26:
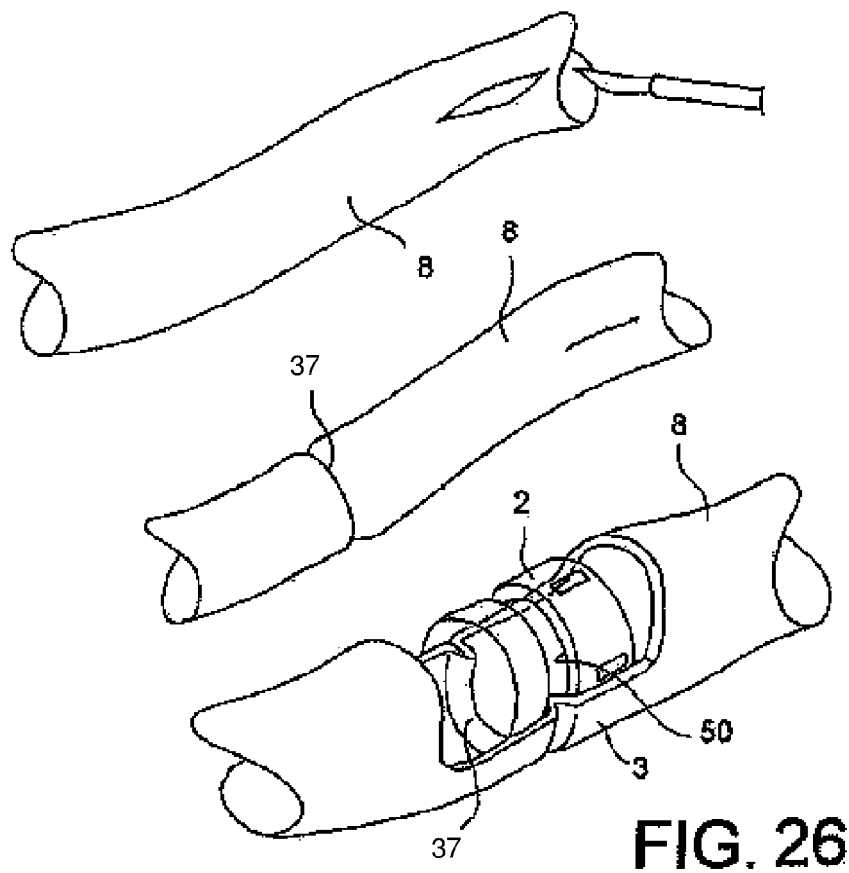
FIGS. 26 and 27 illustrate devices and method steps for anchoring the stimulus device at a target lumen of a gastrointestinal system in accordance with embodiments.
Figure 27:
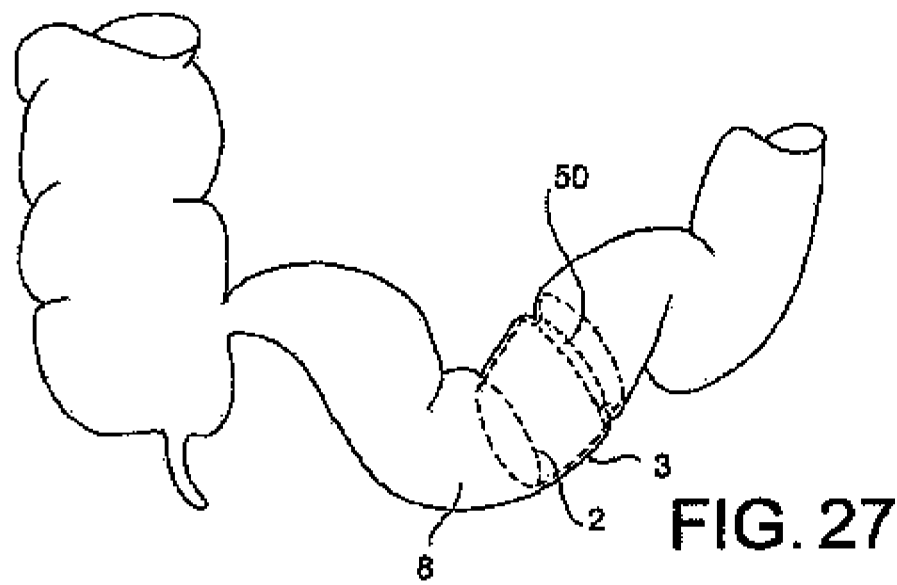
Figure 29:
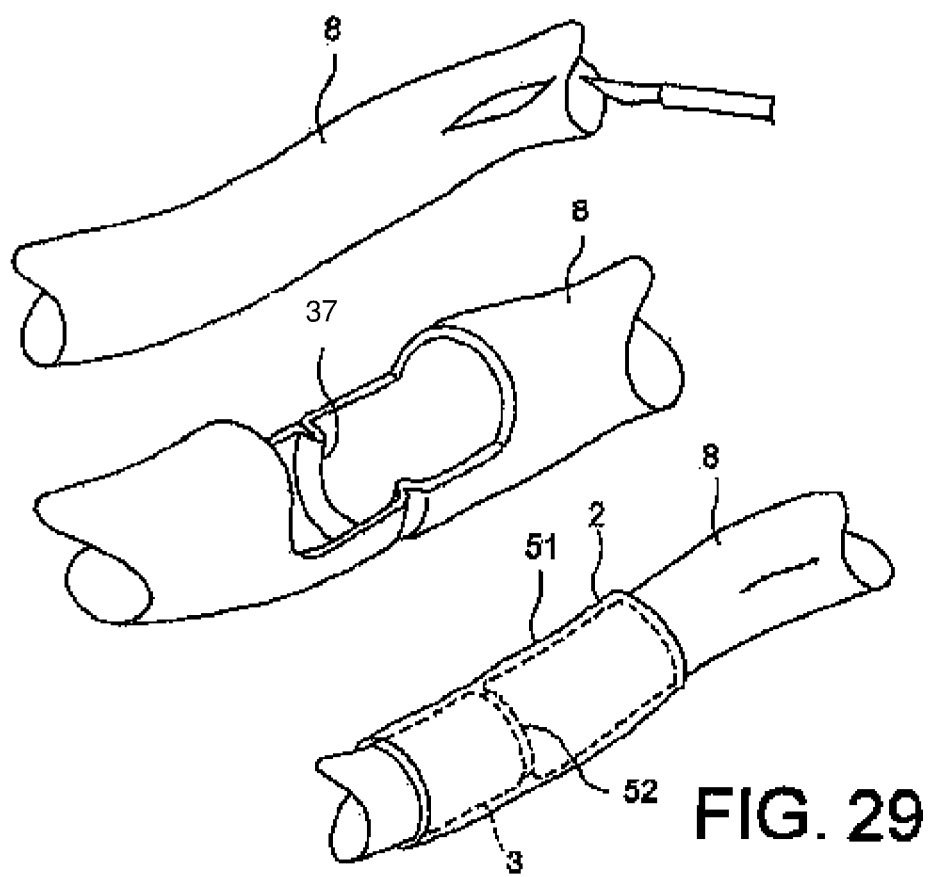
FIG. 29 illustrates devices and method steps for anchoring the stimulus device at a target lumen of a gastrointestinal system in accordance with a further embodiment.

In accordance with embodiments (FIGS. 26, 27, 29), the tissue engaging portion 2 can be anchored in contact with the target tissue 3 by creating, e.g. by means of circular stapling, a circumferential serosa to serosa fold or plication 37 in the ileum or duodenum which can be received in a corresponding groove or which can receive a corresponding ridge of the tissue engaging portion 2.

For this purpose, an endoluminally deployable stimulus device 1 (FIGS. 26, 27) may have a generally tubular shape with an external surface forming the tissue engaging portion 2 and adapted to engage an intestinal mucosa, wherein the external surface forms an externally open circumferential groove 50 which is adapted to receive the plication 37 of the intestinal wall, thereby holding the stimulus device 1 in place.

Alternatively, the stimulus device 1 may comprise a stimulus band 51 (FIG. 29) configured to be deformable from an open shape to a closed ring shape and lockable in the closed ring shape, wherein the tissue engaging portion 2 is arranged at the stimulus band 51 such that it can contact a section of small intestine when the stimulus band 51 is placed from outside around the section of small intestine. The tissue engaging portion 2 may be provided on a radially internal side of the stimulus band 51 to engage the intestine, e.g. the duodenum 7 or ileum 8 from outside. Moreover a ridge 52 can be formed on the internal surface of the stimulus band 51 in a direction that the ridge 52 circumferentially engages the intestinal lumen around which the stimulus band 51 is fastened. With or without meshing with an external groove of the plication 37, the ridge 52 prevents undesired displacement of the stimulus band 51 along the lumen.

Placement of the stimulus band 51 may be effected by open surgery or by laparoscopy, but also by endolumenal transportation of the band 51 to the desired site for stimulating the production of GLP-1, translumenal placement of the band 51 from inside the intestine through an incision in the lumen wall to its outside and extension of the band from outside the lumen around the lumen.

After placement of the stimulus band 51 around the intestine, the tissue engaging portion 2 can be moved to apply the mechanical stimulus from the outside to the tissue.

Figure 28:
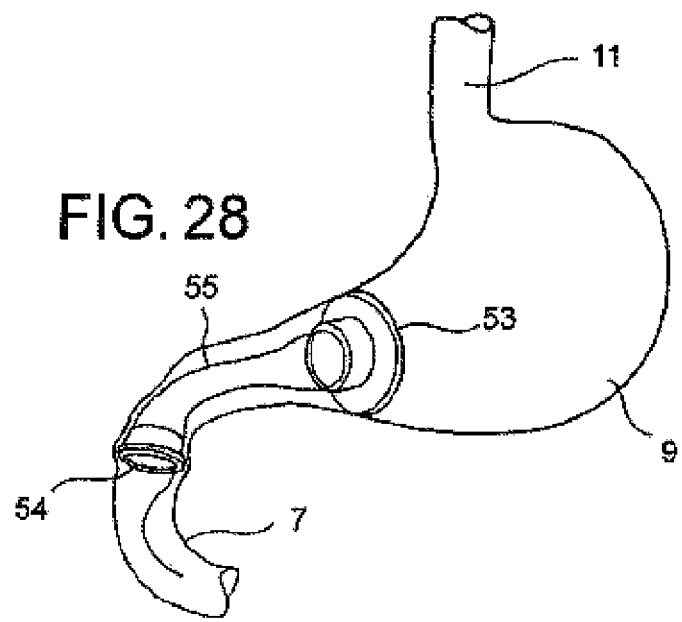
FIG. 28 illustrates devices and method steps for anchoring the stimulus device at a target lumen of a gastrointestinal system in accordance with a further embodiment.
Figure 31:
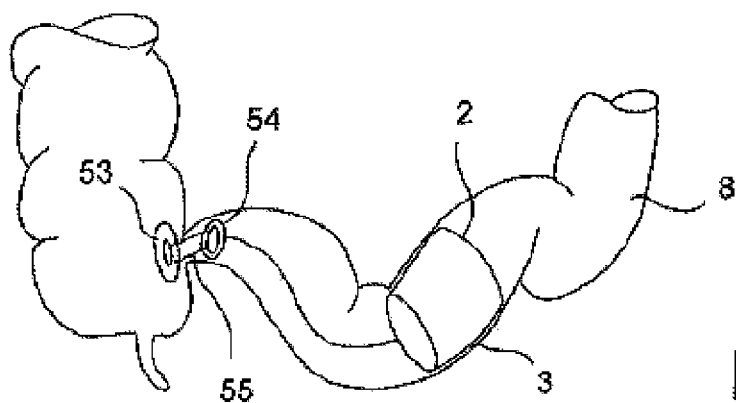
FIG. 31 illustrates devices and method steps for anchoring the stimulus device at a target lumen of a gastrointestinal system in accordance with a yet further embodiment.

In accordance with a further embodiment (FIGS. 28, 31), the anchoring means comprise a proximal annular flange 53 which may be rigid or expandable from an initially collapsed shape, which allows endoluminal insertion thereof into the GI tract, to an expanded shape, which allows the proximal flange 53 to be seated in a first portion of the GI tract. The anchoring means further comprise a distal annular flange 54 which may be rigid or expandable from an initially collapsed shape, which allows endoluminal insertion thereof into the GI tract, to an expanded shape which allows the distal flange 53 to be seated in a second portion of the GI tract divided from the first portion by a restriction of GI wall, e.g. pyloric valve or ileo-cecal valve. The proximal and distal flanges 53, 54 are connected to each other by a pull resistant tether 55 adapted to flexibly extend through the restriction of GI tract, such that the flanges 53, 54 hold the restriction between them. One or both flanges 53, 54 may carry the tissue engaging portion 2 or may provide an anchor to which the tissue engaging portion 2 can be connected e.g. by a tether.

Figure 30:
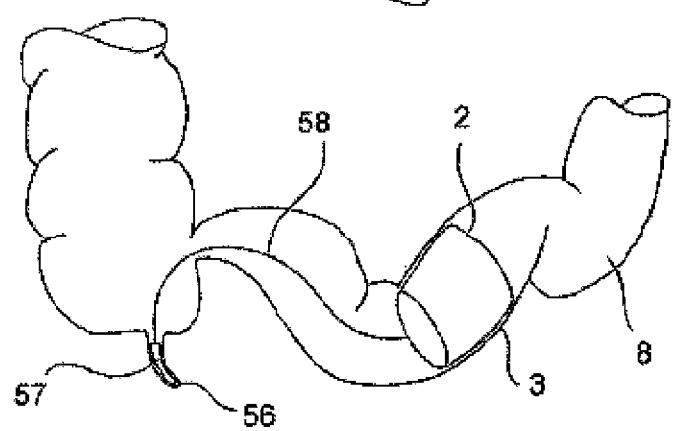
FIG. 30 illustrates devices and method steps for anchoring the stimulus device at a target lumen of a gastrointestinal system in accordance with a yet further embodiment.

In accordance with a yet further embodiment (FIG. 30), the anchoring means may comprise an anchoring hook 57 adapted to be hooked into the appendix 56 and a tether 58 routed through the ileo-cecal valve and connecting the tissue engaging portion 2 (which may stay inside the ileum 8) to the anchoring hook 57.

Figure 32:
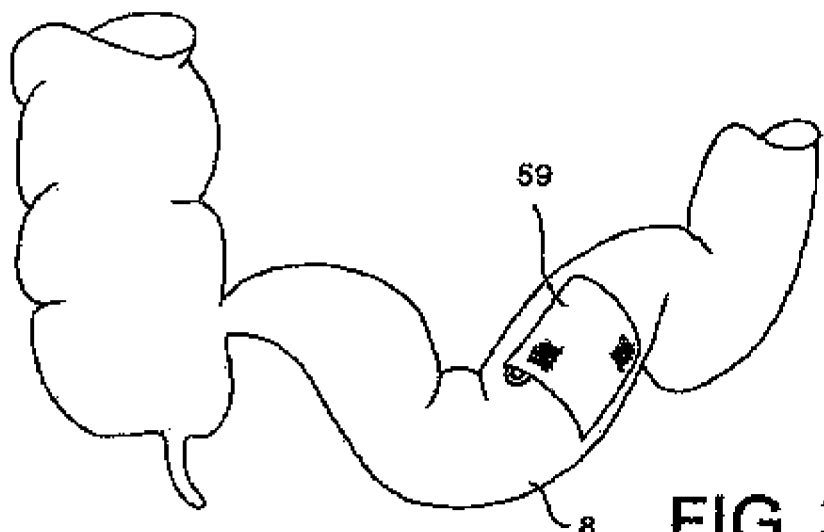
FIG. 32 illustrates devices and method steps for anchoring the stimulus device at a target lumen of a gastrointestinal system in accordance with a yet further embodiment.

In an exemplary embodiment (FIG. 32), a mesh 59 is provided which has attachment loops or attachment portions for a direct attachment of the tissue engaging portion 2 or for the attachment of a tether to anchor the tissue engagement portion 2. The mesh 59 is fastened to the intestinal wall, e.g. by gluing using cyanoacrylate adhesive, and tissue is allowed to grow in the mesh 59 texture to reliably fasten the mesh 59 to the intestine.

Figure 33:
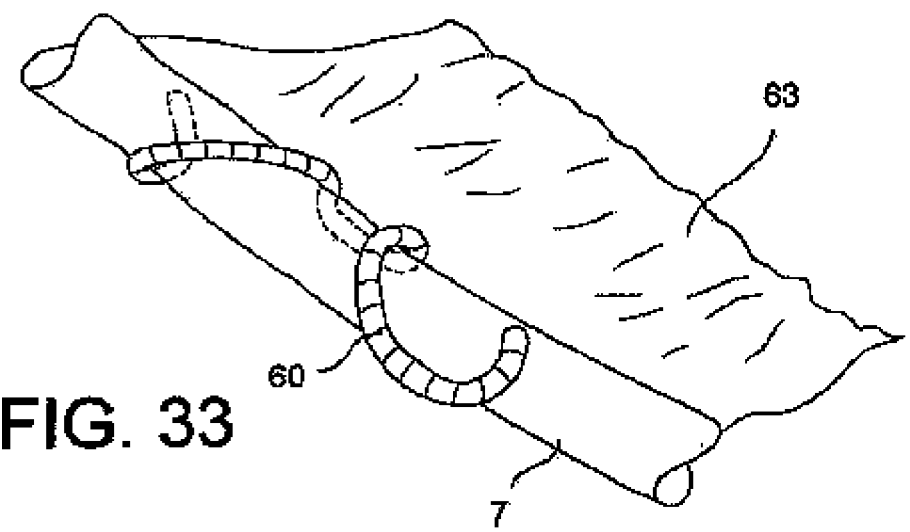
FIGS. 33 and 34 illustrate devices and method steps for anchoring the stimulus device at a target lumen of a gastrointestinal system in accordance with a yet further embodiment.
Figure 34:
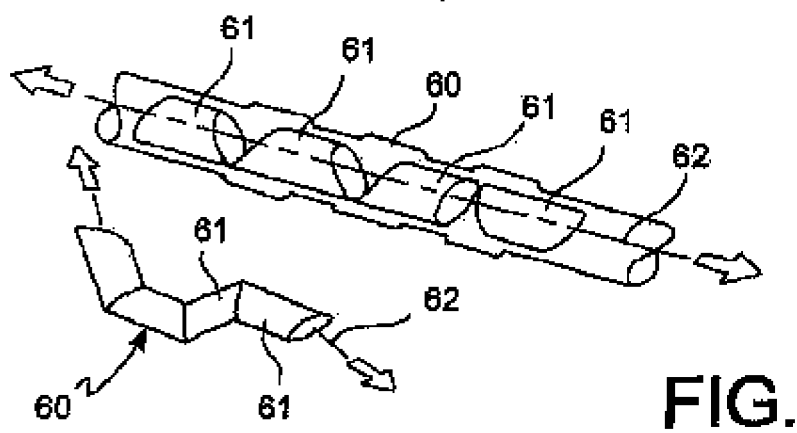

In accordance with a yet further embodiment (FIGS. 33, 34), the anchoring means may comprise an elongate linkage chain 60 comprising a plurality of individual links 61 connected in series and a pull cable 62 which slidingly engages each individual link 61 so that, by pulling the pull cable 62 the links 61 are tightened and aligned together to a predetermined shape so that the linkage chain 60 can be brought from a flexible elongate configuration to a stiff tortuous shape adapted to embrace an intestine from the outside without penetrating the mesentery 63. The tissue engaging portion 2 may be directly or indirectly anchored to the linkage chain 60, e.g. by geometrical coupling through the intestinal wall.

In an alternative embodiment (not illustrated), the anchoring means may comprise a plastically deformable sheet or line-like anchoring member, e.g. in low temperature polymer or thin metal sheet, adapted to be bent around a physiological structure of the subject in a geometrically coupled engagement.

Figures 35, 36:
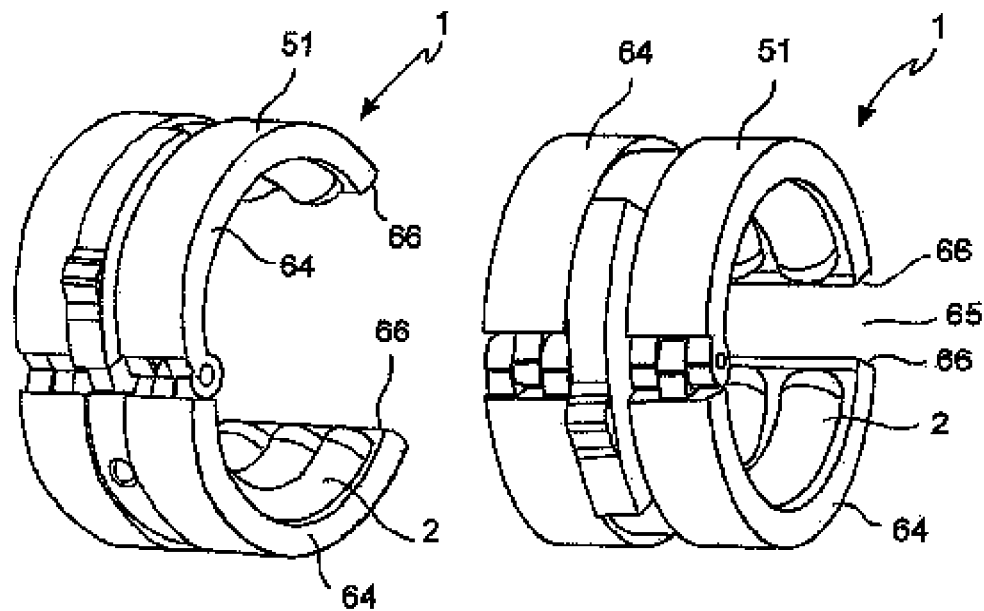
FIGS. 35, 36 and 37 illustrate devices and method steps for anchoring the stimulus device at a target lumen of a gastrointestinal system in accordance with a yet further embodiment.
Figure 37:
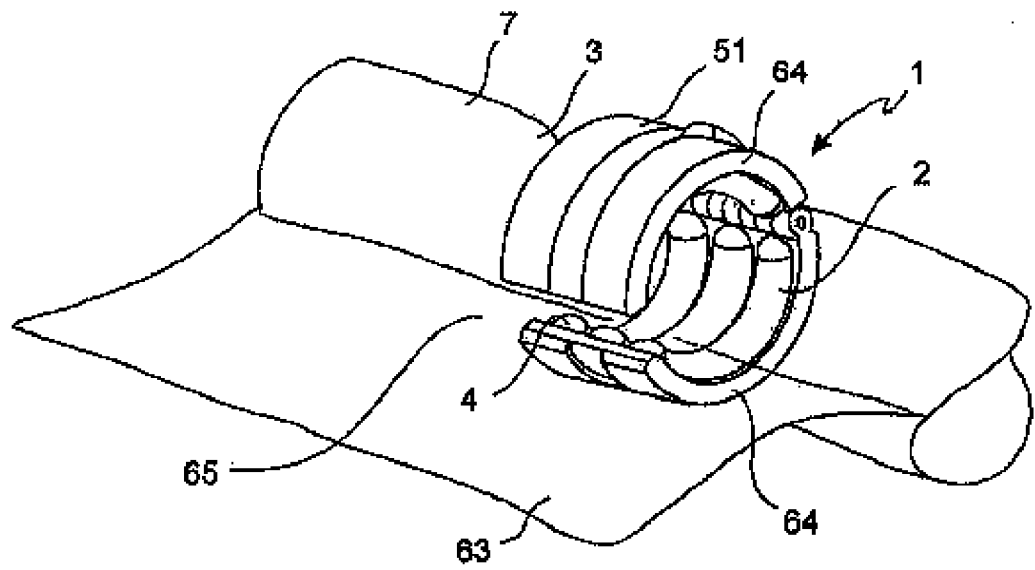

In a yet further embodiment (FIGS. 35 through 37), the anchoring means of the stimulus device 1 may comprise two open arch shaped segments 64 linked together at a first end thereof and lockable and/or elastically biased in an approximated nearly ring shaped closed configuration (FIGS. 36, 37) adapted to embrace a section of intestine from outside, but leaving a free interstice 65 between free ends 66 of the arch shaped segments 64 which allows continuity of mesentery 63 at the target section of intestine.

As will be readily appreciated by those skilled in the art, the present invention address the needs of mini-invasively stimulating an intestinal mucosa to trigger the release of satiety hormone, particularly GLP-1, detecting the ingestion of food for timely stimulating the gut and reliably positioning and anchoring the stimulus device with respect to the desired location for stimulating. Moreover, a closed loop meal detection and intestinal stimulation is provided for a purposeful and timely release of the satiety hormone GLP-1, resulting in an improved glycemic control and an appropriate feel of satiety in T2D and obese patients.

Although preferred embodiments of the invention have been described in detail, it is not the intention of the applicant to limit the scope of the claims to such particular embodiments, but to cover all modifications and alternative constructions falling within the scope of the invention.

The invention claimed is:

1. A system for stimulating the release of satiety hormone in a subject, the system comprising:
   a stimulus device having a tissue engaging portion configured to be placed in contact with a target tissue of a gastrointestinal system of the subject;
   a movement device linked with the tissue engaging portion and operable to move the tissue engaging portion, thereby mechanically stimulating the target tissue; and
   an anchoring device configured to fasten the stimulus device in a target location at the gastrointestinal system such that the tissue engaging portion engages the target tissue;
   wherein the movement device comprises a pump configured to pump a fluid into at least one inflation chamber formed inside the tissue engaging portion, thereby deforming the tissue engaging portion.

2. A system according to claim 1, wherein the pump comprises a compressible fluid chamber in fluidic communication with the inflation chamber, the compressible fluid chamber being connectable to a lumen wall of the gastrointestinal system and configured such that a hoop deformation of the lumen wall brings about a volume change of the fluid chamber, thereby pumping fluid from the fluid chamber into the inflation chamber.

3. A system according to claim 2, wherein the compressible fluid chamber is configured to be locked in an arch or ring shaped configuration and comprises a substantially inextensible radially outer wall and a foldable inner wall such that a displacement of the inner wall in a radially outward direction towards the outer wall reduces an internal volume of the compressible fluid chamber, thereby pumping fluid from the fluid chamber into the inflation chamber.

4. A system according to claim 2, wherein the inflation chamber of the tissue engaging portion is adapted to be locked in an arch or ring shaped configuration and comprises a substantially inextensible radially outer wall and a foldable radially inner wall such that an increase of the internal volume of the inflation chamber displaces the inner wall in a radially inward direction away from the outer wall.

5. A system according to claim 2, wherein the compressible fluid chamber is sized and configured to be endoluminally inserted in a stomach, and the inflation chamber of the tissue engaging portion has a tube shape and is configured to be inserted in a small intestine and comprises a substantially rigid radially inner wall defining a passage for intestinal contents, and a foldable radially outer wall such that an increase of the internal volume of the inflation chamber displaces the outer wall radially outward away from the inner wall.

6. A system according to claim 2, wherein the pump is in fluid connection with an additional fluid reservoir.

7. A system according to claim 2, wherein the pump comprises a manually pressure operable subcutaneously implantable pump.

8. A system according to claim 1, wherein the tissue engaging portion comprises a duodenal sleeve and the at least one inflation chamber is arranged on said duodenal sleeve.

9. A system according to claim 1, further comprising a pH sensor and a control unit linked to the pH sensor and to the pump and configured to activate the pump in response to a detected pH in a predetermined value.

10. A system according to claim 1, further comprising a valve in a fluid duct connecting the pump to the inflation chamber, the valve having flow resistance towards the inflation chamber which is lower than a back flow resistance towards the pump.

11. A system according to claim 1, further comprising an extracorporeal electromagnetic field source, wherein the pump comprises a magnetically attractable component adapted to drive the pump in response to a magnetic field generated by the electromagnetic field source.

12. A system according to claim 1, wherein the inflation chamber comprises an external wall forming inflatable dimples and inextensible wall regions formed around the dimples which do not inflate together with the dimples.

13. A system according to claim 1, wherein the inflation chamber defines a plurality of communicating chamber sections arranged in series and adapted to inflate in a predetermined sequence.

14. A system according to claim 1, wherein the stimulus device comprises two ring members, each having a pressure surface which faces the other ring member and forms one of two opposite lateral faces of an annular groove between the ring members adapted to receive a plication of intestinal wall, wherein the movement device is configured to move the opposite pressure surfaces with respect to each other to apply a mechanical pressure on the plication, wherein at least one of the ring members comprises a rigid backing ring and an inflatable toroidal member connected to the backing ring and forming the pressure surface.

15. A system according to claim 14, wherein the rigid backing rings are movable relative to one another by said movement device.

16. A system according to claim 1, wherein the said stimulus device has a generally tubular shape with an external surface forming the tissue engaging portion and is configured to endoluminally engage an intestinal mucosa, wherein said anchoring device comprises a circumferential groove formed in said external surface and adapted to receive a plication of intestinal wall.

17. A system according to claim 1, wherein the stimulus device comprises a stimulus band configured to be deformable from an open shape to a closed ring shape and lockable in the closed ring shape adapted to externally embrace a section of intestine, wherein the tissue engaging portion is arranged on a radially internal side of the stimulus band.

18. A system according to claim 1, further comprising an implantable detection device configured to continuously monitor at least one physiological characteristic of the subject to detect an ingestion of food, wherein the detection device cooperates with the movement device such that the movement device moves the tissue engaging portion in response to a detected ingestion of food.

19. A method of stimulating the release of satiety hormone in a subject, the method comprising:
    placing a stimulus device in a target location of a gastrointestinal system of the subject such that a tissue engaging portion of the stimulus device engages a target tissue of the gastrointestinal system; and
    deforming and mechanically stimulating the target tissue by moving the tissue engaging portion using a pump that pumps a fluid into at least one inflation chamber formed inside the tissue engaging portion, thereby deforming the tissue engaging portion.

20. A method according to claim 19, further comprising continuously monitoring at least one physiological characteristic of the subject to detect an ingestion of food, wherein the pump moves the tissue engaging portion in response to a detected ingestion of food.

21. A method according to claim 19, wherein the pump comprises a compressible fluid chamber in fluidic communication with the inflation chamber, the compressible fluid chamber being connectable to a lumen wall of the gastrointestinal system and configured such that a hoop deformation of the lumen wall brings about a volume change of the fluid chamber, thereby pumping fluid from the fluid chamber into the inflation chamber.

22. A method according to claim 19, wherein the tissue engaging portion comprises a duodenal sleeve and the at least one inflation chamber is arranged on said duodenal sleeve.

23. A method according to claim 19, further comprising sensing a pH; and
    activating the pump in response to a detected pH in a predetermined value.

24. A method according to claim 19, wherein the pump comprises a magnetically attractable component adapted to drive the pump in response to a magnetic field generated by an extracorporeal electromagnetic field source.

25. A method according to claim 19, wherein the inflation chamber defines a plurality of communicating chamber sections that are arranged in series and that are inflated in a predetermined sequence.

* * * * *